(12) United States Patent
Gokaraju et al.

(10) Patent No.: US 11,707,499 B2
(45) Date of Patent: Jul. 25, 2023

(54) ODOR MASKING FORMULATIONS FOR NATURAL COMPOUNDS

(71) Applicant: LAILA NUTRACEUTICALS, Vijayawada (IN)

(72) Inventors: Ganga Raju Gokaraju, Vijaywada (IN); Rama Raju Gokaraju, Vijayawada (IN); Kishore Babu Govada, Vijayawada (IN); Venkata Krishna Raju Alluri, Vijayawada (IN); Nagendra Babu Vutti, Vijayawada (IN); Kiran Bhupathiraju, Vijayawada (IN); Venkata Kanaka Ranga Raju Gokaraju, Vijayawada (IN); Trimurtulu Golakoti, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 410 days.

(21) Appl. No.: 16/331,370

(22) PCT Filed: Sep. 8, 2017

(86) PCT No.: PCT/IN2017/050388
§ 371 (c)(1),
(2) Date: Mar. 7, 2019

(87) PCT Pub. No.: WO2018/047201
PCT Pub. Date: Mar. 15, 2018

(65) Prior Publication Data
US 2019/0192607 A1    Jun. 27, 2019

(30) Foreign Application Priority Data
Sep. 8, 2016  (IN) .............................. 201641030694

(51) Int. Cl.
A61K 36/84    (2006.01)
A61K 9/14     (2006.01)
A23L 27/00    (2016.01)
A23L 29/288   (2016.01)
A61K 9/00     (2006.01)
A61K 47/38    (2006.01)

(52) U.S. Cl.
CPC .............. *A61K 36/84* (2013.01); *A23L 27/86* (2016.08); *A23L 29/288* (2016.08); *A61K 9/0056* (2013.01); *A61K 9/146* (2013.01); *A61K 47/38* (2013.01); *A23V 2002/00* (2013.01); *A23V 2250/21* (2013.01); *A23V 2300/10* (2013.01); *A23V 2300/31* (2013.01)

(58) Field of Classification Search
None
See application file for complete search history.

(56) References Cited

U.S. PATENT DOCUMENTS

| | | | |
|---|---|---|---|
| 4,313,930 A * | 2/1982 | Wischniewski | A61K 36/48 424/490 |
| 6,346,283 B1 | 2/2002 | Hoffman et al. | |
| 6,413,539 B1 | 7/2002 | Shalaby | |
| 6,419,956 B1 | 7/2002 | Sue et al. | |
| 6,426,112 B1 * | 7/2002 | Boatright | A23L 11/37 426/656 |
| 2016/0089469 A1 | 3/2016 | Wetterer et al. | |

OTHER PUBLICATIONS

Newcomb (Nation Formulary Bull, (1942), vol. 10, pp. 79-83).*

* cited by examiner

*Primary Examiner* — Susan Hoffman
(74) *Attorney, Agent, or Firm* — Kramer & Amado, P.C.

(57) ABSTRACT

The invention discloses odor masking formulations for stench natural compounds, selected from the extracts, fraction and pure phytochemicals that are produced in combination with a natural or synthetic hydrocolloid polymer gum(s). The invention further discloses novel process of producing the odor and taste masking formulations. The invention also discloses taste masking formulations of *valerian* extracts with no characteristic stench odor & or negligible stench odor in combination with natural hydrocolloid gum such as guar gum, acacia or other polymers. The invention further discloses method of reducing insomnia, anxiety, Attention Deficit Disorder (ADD), Chronic Fatigue Syndrome (CFS) using odor masking formulation of the current invention. Importantly, the said odor masked formulation of the present disclosure helps in improving sleep cycle and helps in efficient functioning of brain.

14 Claims, No Drawings

ODOR MASKING FORMULATIONS FOR NATURAL COMPOUNDS

TECHNICAL FIELD OF INVENTION

The invention relates to Odor masking formulations for Obnoxious Odor compounds. In particular, the invention relates to Odor masking formulations for Obnoxious Odor natural compounds comprising extracts, fractions and pure phytochemicals derived from herbs in combination with at least one hydrocolloid polymer of natural or synthetic origin and Gums. The invention further relates to a novel process for producing Odor masked formulations for Obnoxious Odor compounds comprising extracts, fractions and pure phytochemicals derived from herbs in combination with at least one hydrocolloid polymer of natural/synthetic origin and Gums. The invention also relates to odor masked formulations of extracts, fractions or pure compounds of *Valeriana officinalis* in combination with at least one hydrocolloid polymer of natural or synthetic origin and gums. The invention further relates to methods of using *Valerain officinalis* deodorized formulations for the treatment of insomnia, enhancing sleep by reducing anxiety, stress and depression, Attention Deficit Disorder (ADD), Chronic Fatigue Syndrome (CFS) and menopause.

BACKGROUND OF THE INVENTION

Organoleptic properties (especially odor and taste masked) for nutraceutical supplements and drugs have been one of the priority factors for achieving consumer compliance. In case of orally administered products, taste and odor are equally important for patient acceptance and compliance. The difficulty in administration of such supplements or drugs becomes more challenging especially if the drug has similar obnoxious odor causing property post administration as well. So, developing odor and taste masking drug formulations is one of the priority research areas in the field of Pharmaceutical and Nutraceuticals. With ever growing global demand for Nutraceuticals, there has been an overwhelming challenge to develop palatable Nutraceuticals formulations. Various formulation techniques, process optimization and inactive taste and odor masking ingredients were explored by many researchers to address obnoxious odor and bitter taste of drugs and supplements.

*Valerian* of the family Caprifoliaceae is native to Europe, parts of Asia and has naturalized in eastern North America. Various species of *Valerian* were used in the traditional systems of medicine of various countries. The genus contains over 250 species, with many more subspecies. *Valeriana officinalis* (Europe), *V. fauriei* (Chines and Japanese) *V. capensis* (African), *V. edulis* (Mexico) and *V. wallichii* (India) are more prominent species. *Valerian* species are known to possess a wide range of Active Chemical Constituents such as Iridoid valepotriates (valtrates, isovaltrate, didrovaltrate, valerosidate) (0.5%-2.0%), Volatile essential oil (bornyl isovalerenate and bornyl acetate; valerenic, valeric, isovaleric and acetoxy valerenic acids; valerenal, valeranone, cryptofaurinol; and other monoterpenes and sesquiterpenes) (0.2-02.8%). The fresh root does not exhibit odor, while the dried root smells distinctly unpleasant, akin to old gym socks, due to the presence of isovaleric acid. Despite the very effective therapeutic uses attributed to *Valerian* extracts and compounds, the consumer acceptance for those medications is very low due to its offensive odor emitting property pre and post administration.

Many investigations were carried out in order to mask the taste of bitter drugs but very few investigations were carried out in order to mask the offensive odor and significantly less number of investigations were carried out in order to mask both taste and odor in case of obnoxious drugs. Although various taste masking approaches such as Microencapsulation, Coating, Inclusion complexes, Ion exchange, Solid dispersion, pH modification, Adsorption, Gelation, Prodrug approach, Extrusion and Coating were explored, but very few approaches such as coating and adsorption were explored for odor masking.

Hydrocolloids, often called gums, are hydrophilic polymers of vegetable, animal, microbial or synthetic origin that generally contain many hydroxyl groups. Many polyelectrolytes such as Gum Acacia and Uncharged polymer such as Guar Gum have been employed in various odor and taste masking formulations.

WO 2001049270 A2 discloses an odor-masking coating for a pharmaceutical preparation, comprising a coating for masking or reducing the detectable presence of certain characteristic odor or odors, taste or tastes of pharmaceutical preparations, particularly *valerian* extracts. The coating comprises from at least one to three coating compartments, in any combination or as a single-layer amalgam. The first coating compartment preferably comprises hydroxyl alkyl cellulose and an anti-tackiness agent. The second coating compartment preferably comprises a sugar and at least one anti-tackiness agent. The third coating compartment preferably comprises a methacrylate copolymer, hydroxyalkyl cellulose and an anti-tackiness agent. An optional fourth coating compartment may be applied as a cosmetic color coat, need not function as an odor-masking coat, and may be combined with one or more of the other three coating compartments.

EP 0296117 A2 discloses Taste and odor masked edible oil compositions. Pleasant tasting, pleasant smelling edible oil compositions and a process for making the same have been developed. The product comprises unpleasant edible oil and an oil soluble sensory masking agent capable of producing a masking sensation for the unpleasant edible oil. The sensory masking agent is capable of producing a taste masking and/or odor masking sensation for the unpleasant edible oil.

U.S. Pat. No. 5,013,557 discloses a spray-dried spheroidal microcapsule comprising 1-70 wt % sucralphate and 30-99 wt % of a polymer soluble in gastric fluids such as maltrin. The examples illustrate 1:1 sucralfate to maltrin microcapsules, which can be incorporated in chewable products.

U.S. Pat. No. 4,760,093 discloses a taste neutral powder form of spray-dried acetaminophen which consists essentially of about 60% to 74% by weight acetaminophen and about 26% to 40% by weight of a copolymer, cationic in character, based on dimethyaminoethyl methacrylate and neutral methacrylic acid esters.

There is however no prior art, to the best of inventor's knowledge, available on the odor masking of obnoxious odor of the extracts/fractions or pure compounds or Nutraceuticals, because masking of the same is relatively complicated when compared to synthetic drugs.

Moreover, the techniques disclosed in the prior art for synthetic drugs have some inherent disadvantages, which include lack of stability of the formulation resulting in reappearance of obnoxious odor when the odor masked products are subjected to various dosage formulation processes such as capsulation, tableting, suspensions or emulsions and certain physical stress during packaging and handling. In addition, these techniques also affect the stability and bioavailability of the actives.

Therefore there remains a huge need in the art to develop an odor masking formulation, especially to mask the obnoxious odor of natural extracts/fractions or pure compounds or Nutraceuticals.

OBJECT OF THE INVENTION

Therefore the principal object of the present invention is to provide Odor masking formulations of Obnoxious Odor compounds selected from extracts, fractions or pure phytochemicals derived from herbs in combination with at least one hydrocolloid polymer of natural or synthetic origin and Gums.

The further object of the invention is to provide a novel process for producing Odor masked formulations for Obnoxious Odor compounds comprising extracts, fractions or pure compounds derived from herbs in combination with at least one hydrocolloid polymer of natural/synthetic origin and Gums.

Another object of the invention is to provide odor masked formulations comprising extracts, fractions or pure compounds selected from the group consisting of *Valerian officinalis, Valerian walachi, Murraya koenigii* and *Moringa oleifera* in combination with at least one hydrocolloid polymer of natural or synthetic origin and gums.

The other object of the present invention is to provide methods of using *Valerain officinalis* deodorized formulations for the treatment of insomnia, enhancing sleep by reducing anxiety, stress and depression, Attention Deficit Disorder (ADD), Chronic Fatigue Syndrome (CFS) and menopause.

SUMMARY OF THE INVENTION

The major aspect of the present invention is to provide Odor masking formulations of Obnoxious Odor compounds selected from the extracts, fractions or pure compounds derived from herbs in combination with at least one hydrocolloid polymer of natural or synthetic origin and Gums.

The obnoxious odor compounds as referred herein and throughout the specification means and include nutraceutical or dietary supplements.

The herbs containing the obnoxious odor compounds are, for example, may be selected from the group consisting of *Valerian officinalis, Valerian walachi, Murraya koenigii* and *Moringa oleifera*.

The other important aspect of the present invention is to provide a novel process for producing Odor masked formulations for Obnoxious Odor compounds comprising extracts, fractions or pure compounds derived from herbs in combination with at least one hydrocolloid polymer of natural/synthetic origin and Gums.

Another aspect of the invention is to provide odor masked formulations comprising extracts, fractions or pure compounds selected from the group consisting of *Valerian officinalis, Valerian walachi, Murraya koenigii* and *Moringa oleifera* in combination with at least one hydrocolloid polymer of natural or synthetic origin and gums.

The other aspect of the present invention is to provide methods of using deodorized formulations for the extracts, fractions or pure compounds derived from *Valerain officinalis* for enhancing sleep, reducing anxiety, stress and depression, treating insomnia, Attention Deficit Disorder (ADD), Chronic Fatigue Syndrome (CFS) and menopause.

DETAILED DESCRIPTION OF THE INVENTION

Drug or active as used herein refers to phytochemical(s) in the extracts, fractions or pure compounds, which cause obnoxious odor.

Herbal products have become very popular during the recent years as consumers are looking for natural and traditional alternatives for modern medicines. Phytochemicals are natural compounds found in plants and are responsible for providing color, flavor, and aroma to fruits and vegetables. The phytochemicals include phenols and polyphenols, alkaloids, flavonoids, isoflavones, terpenes, and glucosinolates. However, most, if not all, of these bioactive compounds generally comes with very poor organoleptic properties such as obnoxious odor, bitter, acrid, or astringent taste and therefore unpalatable to the consumer necessitating the need for deodorizing/masking the obnoxious odor and bitterness of the ingredients. As a result, the food and supplement industry either routinely removes these compounds from plant foods or adopt a variety of deodorizing or debitterizing techniques for improving the consumer acceptance.

For the purpose of the present invention, the herbs containing the obnoxious odor compounds are, for example, may be selected from the group consisting of *Valerian officinalis, Valerian walachi, Murraya koenigii* and *Moringa oleifera*.

Extracts of *Valerian* species, especially *Valerian officinalis* and *Valerian wallachi* are a few such plant products with potential applications for insomnia in traditional medicine as a sleep aid. Its supplementation is known to reduce anxiety, stress and improve sleep cycle. Its efficacy is well proven by numerous human clinical trials. Unfortunately, the extracts of *Valerian* are very obnoxious in odor and highly unpalatable and this has become a potential limitation for its use in medicine and food formulations.

A natural *Valerian officinalis* extract standardized to 0.8% valerenic acids (LN16017) and, a natural *Valerian walachi* extract standardized to 20% of total valproates (LN16018) by volumetric method of analysis are used for demonstrating the invention. Various Hydrocolloid gums having properties, such as but not limited to swelling, water absorbing, water holding, three dimensional network formation, viscosity enhancement, hydrogen bonding, and presence of polyelectrolytes can be used for masking the odor and taste of the *Valerian* extracts.

By understanding the chemistry of the *Valerian* actives and physiology of olfactory receptors, the offensive odor of LN16017 or LN16018 is modified or masked by the following approaches such as—
1. Entrapping the odor causing molecule in three dimensional gel networks.
2. Reducing the effective surface area of odor causing drug material.
3. Reducing the diffusion of odor causing molecules by increasing the viscosity of the hydrated formulations.

Odor masking using different types of technologies such as Microencapsulation, Coating, Inclusion complexes, Ion exchange, Solid dispersion, pH modification, Adsorption, Gelation, Prodrug approach, Extrusion and Coating techniques are currently in use. Though each of these techniques has some unique advantages, they suffer from some inherent disadvantages as well. For example, 1) reappearance of obnoxious odor or bitterness when breaking of granules prepared by Granulation technique occur during the process of compression or shipping, improper coating and lack of robust film coating by Coating technique, 2) Possible cross reaction may occur between core and wall material and difficulty in achieving continuous and uniform film by Microencapsulation technique, 3) Most of the polymers used in Solid dispersions technique can absorb moisture, which may result in phase separation, crystal growth or conversion from the amorphous to the crystalline state or from a metastable crystalline form to a more stable structure during storage, 4) The toxicity associated with the coating or complexing agent such as cyclodextrin (e.g., DM-β-CD) has often been a concern. 5) Also there could be issues with the stability of the active in odor masked formulations during its transport across the gut.

The inventors have conducted research studies to develop an odor masking formulation without the said disadvantages for extracts, fractions and pure compounds of plant origin with Stench odor. It was found surprisingly that the odor masking formulation of odor causing compounds when produced in combination with hydrocolloid(s) or gum(s) of vegetable, animal, microbial or synthetic origin that generally contains many hydroxyl groups and some of them may be poly electrolytes, using a novel process, showed unique properties and the formulations thus produced are completely devoid of the inherent obnoxious odor.

Thus in a preferred embodiment, the present invention provides an odor masked nutraceutical formulations which comprises at least one obnoxious or stench odor compound and at least one hydrocolloid polymer of natural or synthetic origin, wherein the ratio of active to polymer is in the range of 1:10 to 10:1.

The obnoxious and stench causing natural compound according to the invention may be selected from the extracts, fractions, pure phytochemical or their compositions derived from the plant parts of *Valerian officinalis, Valerian walachi, Murraya koenigii* and *Moringa oleifera*.

The invention is further illustrated below taking *valerian officinalis* extract LN16017 as an example for obnoxious compound and Guar gum or gum acacia as hydrocolloid polymers for the preparation of odor and taste masking formulation. The extract of *Valerian officinalis* is standardized to 0.01% to 30% total valerinic acids.

*Valerian officinalis* alcohol extract (LN16017) is a water miscible extract. All hydrocolloids interact with water, reduces its diffusion and stabilizes its presence. The stabilizing of water occurs due to entrapment of water molecules within the three dimensional network of gel. Addition of *valerian* extract LN16017 to hydrated gum employing suitable planetary mixer helps in equal and uniform distribution of extract within the gel. The mixing process helps in disruption of three dimensional networks and penetration of drug molecules into the core of three dimensional networks. The pseudoplastic rheological behaviors (Gel-Sol) of hydrocolloids help in shear thinning of gel which facilitates uniform mixing. Upon complete uniform mixing, the removal of shear stress (mixing in this case) causes the gel viscosity to increase due to thixotropic behavior (Sol-Gel). The increased viscosity results in reformation of three dimensional networks leading to entrapment of water losing it's ability to flow. This entire phenomenon helps in locking the odor causing drug molecules, reduction of evaporative surface area and increase in viscosity leading to successful stench odor masking of *valerian* extract.

Upon drying of the above *valerian* gel the water evaporates leading to conformationally rigid colloid with decreased chain length which completely encloses/encapsulates the odor causing molecules, thus leading to odor masked products.

The said Odor masking formulation of *valerian* extract, which addresses all the disadvantages mentioned in the existing literature, is innovative as the current method uses the concept of Reduced evaporative surface area, Reducing diffusion of odor causing molecules by increasing the viscosity of the hydrated formulations and entrapment of drug molecules within three dimensional network in addition to creating a barrier between active stench odor compounds and olfactory, receptors thus effectively achieving the odor masking.

This novel process eliminates the intensity of stench odor of natural plant extracts by a simple entrapment process, which occurs at micro and nano molecular level of drug molecules. Hence free drug available at different micron sizes are reduced which eliminates the stench odor generally associated with other techniques.

This process of odor masking approach requires following basic materials & equipment's.

Materials:
1. Solvent (water)
2. Hydrocolloid Gum (Guar gum, Gum acacia, Gum Kondagogu, Gum Karaya, Xanthum gum, carrageenan, sodium alginate, locust bean gum, gum ghati, carbopol, Tragacanth, Semi synthetic & synthetic celluloses) and optionally
3. Cross linking agents (gelatin, formaldehyde, glutaraldehyde, Calcium chloride, and other strong electrolyte solutions)
4. Natural & Artificial Preservatives
5. Natural & artificial flavors Equipment:
1. Planetary mixer
2. Vacuum dryer
3. Miller.
4. Sifter.

According to the invention a presoaked hydrocolloid polymer/gum in water was transferred into planetary mixer and suitable quantity of *valerian* extract LI16017 was added under continuous mixing at 50 rpm. The uniform mixing helps in penetration of extract into three dimensional gel network and entraps the odor causing molecules. Mixing is continued until homogenous gel extract mixture was obtained. The product was collected into stainless steel trays and dried in vacuum dryer. The flakes were collected, milled and sifted through a suitable sieve to obtain odor and taste masked product of *Valerian* as a powder.

Even though the above technique has been demonstrated taking *Valerian officinalis* extract as an example, it can be applied to obnoxious odor causing extracts, fractions and pure compounds derived from any *Valerian* species, which include *Valeriana wallachi* and *Valeriana officianalis* or any other odor causing material derived from plants such as *Murraya koenigii* and *Moringa oleifera* using a proper selection of suitable hydrocolloid gums, preservatives, flavoring agents and equipment. This process of odor masking eliminates the process of evaporation & diffusion of the drug to occur as there is formation of strong, three dimensional networks around the drug molecules which further decreases the effective surface area of active compounds available for evaporation/diffusion which in turn achieves the targeted products which are deodorized. Hence the availability of free drug for evaporation/diffusion is reduced. As the entrapment is strong there is no possibility of losing the deodorization effects during the process of compaction or any other physical process operations.

Accordingly, in the primary embodiment, the invention provides an odor masking formulation for obnoxious & stench compounds comprising an odor causing compound ingredient selected from the extracts, fractions and pure phytochemical derived from plant raw materials and a hydrocolloid polymer(s) selected from natural polymer(s) or synthetic cationic polymer(s), wherein the formulation is obtained through a novel process involving hydration/solvation hydro colloidal polymer, mixing the said Hydrogel/Organogel with the obnoxious and/or stench causing natural compound and drying the mixture to result in entrapment of odor causing molecules within the three dimensional polymer networks in a close proximity.

In other important embodiment, the invention provides a process for producing odor masking formulations, which comprises the steps of a) hydration/solvation of the hydro colloid polymer with suitable volumes of water/solvent under vigorous stirring; b) Mixing of obnoxious compound in completely hydrated polymer solution under Planetary mixer (150-300 RPM), wherein the ratio between the obnoxious compound and polymer is in the range of 1:10 to 10:1, to obtain homogenous, viscous gel of the compound and polymer; c) drying the said hydrogel of polymer and obnoxious compound using vacuum dryer at 40-80° C.; d) pulverizing the flakes and sieving the powder through appropriate mesh to obtain odor & taste masking formulation as granules of uniform size.

In other important embodiment, the invention provides a process for producing odor masking formulations for obnoxious & stench compounds, where in the obnoxious & stench compounds can be selected from the list comprising the extracts, fraction, pure compounds derived from *Valeriana wallachi* and *Valeriana officianalis* or any other odor causing material derived from plants such as *Murraya koenigii* and *Moringa oleifera*.

In one embodiment odor masking is achieved using different types of hydrocolloid polymer gums or polyelectrolyte containing gums selected from natural and synthetic origin such as but not limited to Guar gum, Gum acacia, Gum Kondagogu, Gum Karaya, Xanthum gum, carrageenan, sodium alginate, locust bean gum, gum ghati, carbopol, HPMC, Tragacanth, Semi synthetic & synthetic celluloses or mixtures thereof. The natural polymer may be selected from polyelectrolyte (Marine source: Agar, Aliginic acid & its salts, carrageenan) (Plant source: Gum Arabic, Gum Ghati, tragacanth, karaya gum), or uncharged (Guar gum, locust bean gum, Oat gum, chicle gum, dammer gum, mastic gum, *Psyllium* seed husk, tara gum etc) The odor masked formulations thus obtained show different levels of odor masking, as well as drug release, and site specific drug delivery.

In another embodiment, the solvent used for preparing gel is selected from water, ethanol, methanol, isopropyl alcohol and ethyl acetate, or mixtures thereof etc. based on the gelling nature of the polymer employed. The solvent used for preparing polymeric solution is based on selection of polymer for desired site of action. The type of solvent used for preparing polymer-drug solution is based on gelling nature of the polymer.

In yet another embodiment, the invention provides a process for the preparation of odor & taste masking formulation through hydration/solvation of gum to increase flexibility of the polymer, mixing of gel with drug/active extracts/fractions/compounds by the means of planetary mixer, evaporation of the solvent used for swelling, which comprises the steps of;

a) preparing the hydrated hydrocolloid polymer/gum solution;
b) adding slowly drug/active extracts/fractions/compounds to the completely hydrated and swollen gel using planetary mixer at suitable RPM (100-300);
c) drying the formulation through the process of removing the solvent under vacuum and drying at 25-100° C. for 1-5 hours to obtain dried flakes;
d) Pulverizing the dried flakes, blending the powder to obtain homogenous powder and
e) sifting the formulation through 20-120 # mesh to obtain uniform granules or powder of odor masked drug/active extracts/fractions/compounds.

In another embodiment, invention provides odor/taste masking formulations, which optionally comprise at least one inert ingredient/excipient/carrier(s) selected from disintegrates, glidants, lubricants, diluents, or preservatives.

In a further embodiment, the invention provides dosage forms containing the above odor formulations, wherein the dosage forms include different types of tablets (such as oro dispersible tablets, chewable tablets, effervescent and non-effervescent tablets, sublingual tablets, buccal tablets and also site specific drug delivery tablets), capsules, liquid dosage forms (such as suspensions, solutions, beverages), semisolid, food and confectionary, milk products, etc.

In another embodiment, the percentage of hydro colloid polymer in the polymer-drug gel solution can vary in the range of 10-80%. The % of solvent is selected based on required viscosity and gelling behavior of drug-polymer solution.

In another embodiment, the ratio between the drug/active and the polymer in the odor masking formulation varies in the range of 10:1 to 1:10, and the ratio between the solvent used for dissolving the polymer and the drug/active varies in the range from 1:0.1 to 1:100, and the ratio between the polymer and solvent is in the range of 1:1 to 1:60.

In other embodiment, the odor masking formulation for obnoxious compounds, wherein the compounds are of phytochemical origin, selected from extracts, fractions or pure phytochemicals derived from plants, which include but not limited to compounds containing volatile oils, glycoside and their derivatives, terpenes, sterols or steroids, saponins, alkaloids, tannins, polyphenols, proanthocyanidins, flavonoid and other category of extracts.

In other embodiment, the current odor masking formulations can be used for making dosage forms, which include tablets of different type such as enteric coated granules or tablets, chewable formulations, gummy snacks, colon targeted granules, pH dependent drug release based on site specific delivery of liquid orals such as suspensions, solutions, beverages of different types.

In another embodiment, the invention provides the method of use of the odor masking formulations prepared from *valerian* extract in a subject or a warm blooded animal for improving sleep cycle/brain health; reducing anxiety, reducing Attention Deficit Disorder (ADD), Chronic Fatigue Syndrome (CFS), wherein the method comprises supplementing the said subject or warm blooded animal with an effective dose of odor masking formulations comprising *Valerian* extract or their compositions and hydrocolloid polymer(s) of synthetic or natural origin.

In another embodiment, the dose of final formulation is based on type of dosage form (solid dosage forms. liquid dosage forms, food products, beverages, confectionaries) and age group and different races of population, wherein the general solid dosage form varies in the range between 25-3000 mg in single or divided doses. This technique of odor masking also reduces the evaporation of volatile oils such as isovaleric acid in this case, in addition to reducing the surface area of drug molecules for interaction with odor receptors. These types of reducing volatility/preventing drug interaction with odor receptors itself reduce the intensity of stench compounds.

In one important embodiment, the formulation further contains flavoring agent optionally selected from Ginger oil, Raspberry oil, vanilla essence, orange oil, Tea tree oil, etc.

The following examples, which include preferred embodiments, will serve to illustrate the practice of this invention, and it being understood that the particulars shown are by way of example and for purpose of illustrative discussion of preferred embodiments of the invention and they are not to limit the scope of the invention.

Example 1

Dried roots of the plant material *Valeriana officinalis* (100 g) were pulverized to coarse powder, extracted with ethyl alcohol (300 mL) at a temperature range of 65-70° C. for 2 hrs. Extraction process repeated thrice using 250 mL of ethyl alcohol each time with respect to plant material. All the three extracts were combined, the mixture was fine filtered and concentrated under vacuum at 40-50° C. to get *Valeriana officinalis* alcohol extract 0.01% to 30% total valerenic acids (LN16017) as a Thick paste (16 g).

Example 2

Dried roots of the plant material *Valeriana wallichii* (100 g) were pulverized into a coarse powder and extracted with water (300 mL) at 80-85° C. for 2 hrs. Extraction process was repeated four times using 250 mL water each time and the extracts were combined, the combined aqueous extract was fine filtered and the clear extract was concentrated on a climbing film evaporator at 50-60° C. under reduced pressure to obtain *Valeriana wallichii* water extract (LN16018) as dry powder (25 g).

Example 3

Process for Preparation of Odor Masking Formulations
Procedure:—
1) Transferred 30 ml of water in to a clean and dry open vessel with stirrer.
2) To this added 1 g of Xanthan gum under low stirring and allowed the contents to mix well. The gum phase was kept for soaking at room temperature for overnight in order to completely hydrate the gum phase in water. The ratio of gum:solvent can vary depend on type of gum and its swelling index, therefore the volume of solvent used for soaking can vary between 1:1.5 to 1:60
3) Mixed well the contents of gum phase (after completion of soaking) to obtain homogenous gum phase in to which added under continues stirring 1 g of LN 16017 to obtain homogenous uniformly distributed drug-gummy solution.
4) After uniform mixing loaded the sample for drying at 40-80° C. to obtain dried mass.
5) Pulverized and sifted the contents through required sieve to obtain homogenous, free flowing powder blend of formulation-1.

The aforementioned process is followed to prepare various odor masked formulations using different solvent extracts, hydro colloidal polymers, and solvents with different ratios and the data is summarized in tables 1-4.

TABLE 1

Odor masked formulations of LN16017 with different natural gums

| S. NO | Formulation# | LN16017 (gm.) | Xanthan gum | Carrageenan | Gum Kondagogu | Gum Karaya | Gum *Acacia* | Guar Gum | Water |
|---|---|---|---|---|---|---|---|---|---|
| 1 | Formulation-1 | 1 g | 1 g | | | | | | 30 ml |
| 2 | Formulation-2 | 1 g | | 1 g | | | | | 30 ml |
| 3 | Formulation-3 | 1 g | | | 1 g | | | | 30 ml |
| 4 | Formulation-4 | 1 g | | | | 1 g | | | 20 ml |
| 5 | Formulation-5 | 1 g | | | | | 1 g | | 3 ml |
| 6 | Formulation-6 | 1 g | | | | | | 1 g | 30 ml |

TABLE 2

Odor masked formulations of LN16017 with different ratios of Active and Gum

| S. NO | Formulation# | LN16017 (gm.) | Gum *acacia* (gm) | Guar gum (gm) | Water (ml) | Active:Gum ratio |
|---|---|---|---|---|---|---|
| 1 | Formulation-7 | 0.125 | 12.5 | | 18.5 | 0.1:10 |
| 2 | Formulation-8 | 20.88 | 4.12 | | 185 | 5:1 |
| 3 | Formulation-9 | 4.12 | 20.88 | | 18.5 | 1:5 |
| 4 | Formulation-10 | 12.5 | 0.125 | | 185 | 10:0.1 |
| 5 | Formulation-11 | 0.125 | | 12.5 | 37.5 | 0.1:10 |
| 6 | Formulation-12 | 20.88 | | 4.12 | 375 | 5:1 |
| 7 | Formulation-13 | 4.12 | | 20.88 | 37.5 | 1:5 |
| 8 | Formulation-14 | 12.5 | | 0.125 | 375 | 10:0.1 |

TABLE 3

Odor masked formulations of LN16017 with different ratios of Gum and water

| S. NO | Formulation# | LN16017 (gm.) | Gum acacia (gm) | Guar gum (gm) | Gum karaya | Water (ml) | Gum:water ratio |
|---|---|---|---|---|---|---|---|
| 1 | Formulation-15 | 12.5 | 12.5 | | | 18.5 | 1:1.5 |
| 2 | Formulation-16 | 12.5 | | 12.5 | | 187.5 | 1:15 |
| 3 | Formulation-17 | 12.5 | | | 12.5 | 18.5 | 1:1.5 |
| 4 | Formulation-18 | 12.5 | 12.5 | | | 37 | 1:3 |
| 5 | Formulation-19 | 12.5 | | 12.5 | | 375 | 1:30 |
| 6 | Formulation-20 | 12.5 | | | 12.5 | 37 | 1:3 |
| 7 | Formulation-21 | 12.5 | 12.5 | | | 74 | 1:6 |
| 8 | Formulation-22 | 12.5 | | 12.5 | | 750 | 1:60 |
| 9 | Formulation-23 | 12.5 | | | 12.5 | 74 | 1:6 |

TABLE 4

Odor masked formulations of different solvent extracts with different gums

| S. No | Ingredients | Formulation-24 | Formulation-25 | Formulation-26 | Formulation-27 | Formulation-28 | Formulation-29 |
|---|---|---|---|---|---|---|---|
| 1 | Gum acacia | 2.5 g | | 2.5 g | | 2.5 g | |
| 2 | Carbopol 974 P | | 2.5 g | | 2.5 g | | 2.5 g |
| 3 | Valeriana officinalis Acetone extract | 2.5 g | 2.5 g | | | | |
| 4 | Valeriana officinalis Ethyl acetate extract | | | 2.5 g | 2.5 g | | |
| 5 | Valeriana officinalis Ethanol extract | | | | | 2.5 g | 2.5 g |
| 6 | Water | 7.5 mL | 50 mL | 7.5 mL | 50 mL | 7.5 mL | 50 mL |
| 7 | Flavouring agent | 0.05 g | 0.05 g | 0.05 g | 0.05 g | 0.05 g | 0.05 g |

TABLE 5

Experiments with LN16018 with 3 different natural gums

| S. No | Ingredient | Batch No | Formulation -30 | Formulation -31 | Formulation -32 |
|---|---|---|---|---|---|
| 1 | LN16018 | CLM16010015 | 12.5 g | 12.5 g | 12.5 g |
| 2 | Gum Acacia | 1098-0598-2609-13 | 12.25 g | | |
| 3 | Guar gum | KBP-35 | | 12.25 g | |
| 4 | Gum Karaya | KBP-0.3.2/3.1/7 | | | 12.25 g |
| 5 | Water | NA | 37 g | 375 g | 37 g |
| 6 | Flavouring agent | AR2410 | Q.S | Q.S | Q.S |

Analytical Studies

Among the prepared odor masked formulations selected formulations were further analysed using validated HPLC method in order to check the effect of process on active constituents of extracts. A total of three analyte markers such as Hydroxy valerenic acid, Acetoxy valerenic acid and Valerenic acid and the total valerenic acids were analysed. The details of analytical results obtained are given in table 6. From the analytical results it is evident that the method does not interfere with active constituents and sufficient assay was observed in the formulations.

TABLE 6

Analytical results for odour masked formulations

| S. No | Batch No | % Hydroxy valerenic acid | % Acetoxy Valerenic acid | % Valerenic acid | % Total valerenic acid |
|---|---|---|---|---|---|
| 1 | Formulation 24 | 0.118 | 0.601 | 0.622 | 1.341 |
| 2 | Formulation 25 | 0.098 | 0.492 | 0.506 | 1.096 |
| 3 | Formulation 26 | 0.046 | 0.179 | 0.226 | 0.45 |
| 4 | Formulation 27 | 0.057 | 0.161 | 0.259 | 0.48 |
| 5 | Formulation 28 | 0.124 | 0.697 | 0.673 | 1.49 |
| 6 | Formulation 29 | 0.056 | 0.292 | 0.274 | 0.62 |

Odour Masking Studies

Odour evaluation studies were carried out in order to evaluate the odour masking effect of the technique. The study was conducted for all formulations. A total of 3 volunteers have participated in the study. Based on the olfactory stimuli felt by the volunteer a suitable scoring is given as per following table.

TABLE 7

Odour intensity referring scale

| S. NO | Odour intensity | Score |
|---|---|---|
| 1 | Very faint and not annoying | 1 |
| 2 | Faint and a little annoying | 2 |
| 3 | Noticeable and annoying | 3 |
| 4 | Strong and very annoying | 4 |
| 5 | Extremely annoying | 5 |

Good odour masking was achieved with all experiments given in table-2 to table-6.

TABLE 8

Odour masking report

| S. No | Formulation No | Voluntary-1 | Voluntary-2 | Voluntary-3 |
|---|---|---|---|---|
| 1 | Formulation-1 | 1 | 2 | 1 |
| 2 | Formulation-2 | 2 | 1 | 2 |
| 3 | Formulation-3 | 2 | 2 | 2 |
| 4 | Formulation-4 | 2 | 1 | 1 |
| 5 | Formulation-5 | 3 | 1 | 1 |
| 6 | Formulation-6 | 1 | 1 | 3 |
| 7 | Formulation-7 | 1 | 1 | 3 |
| 8 | Formulation-8 | 1 | 3 | 1 |
| 9 | Formulation-9 | 1 | 1 | 1 |
| 10 | Formulation-10 | 3 | 3 | 2 |
| 11 | Formulation-11 | 1 | 2 | 3 |
| 12 | Formulation-12 | 1 | 1 | 1 |
| 13 | Formulation-13 | 1 | 1 | 2 |
| 14 | Formulation-14 | 2 | 1 | 1 |
| 15 | Formulation-15 | 1 | 1 | 1 |
| 16 | Formulation-16 | 2 | 1 | 1 |
| 17 | Formulation-17 | 1 | 1 | 2 |
| 18 | Formulation-18 | 1 | 2 | 1 |
| 19 | Formulation-19 | 1 | 1 | 1 |
| 20 | Formulation-20 | 1 | 1 | 1 |
| 21 | Formulation-21 | 3 | 2 | 1 |
| 22 | Formulation-22 | 1 | 1 | 1 |
| 23 | Formulation-23 | 1 | 3 | 1 |
| 24 | Formulation-24 | 1 | 2 | 1 |
| 25 | Formulation-25 | 2 | 1 | 1 |
| 26 | Formulation-26 | 1 | 1 | 1 |
| 27 | Formulation-27 | 1 | 1 | 1 |
| 28 | Formulation-28 | 2 | 1 | 2 |
| 29 | Formulation-29 | 1 | 1 | 1 |
| 30 | Formulation-30 | 1 | 1 | 1 |
| 31 | Formulation-31 | 1 | 1 | 1 |
| 32 | Formulation-32 | 1 | 1 | 2 |

We claim:

1. An odor masked nutraceutical or dietary supplement formulation comprising an obnoxious or stench causing natural compound and a hydrocolloid polymer of synthetic or natural origin;
   wherein:
      the obnoxious or stench causing natural compound is selected from the group consisting of a valerenic acid, an extract of *Valeriana officinalis*, an extract of *Valeriana wallichii*, an extract of *Murrava koenigii*, an extract of *Moringa oleifera*, and combinations thereof;
      the hydrocolloid polymer is selected from the group consisting of Guar gum, Gum acacia, Gum Kondagogu, Gum Karaya, Xanthum gum, carrageenan, sodium alginate, locust bean gum, gum ghati, carbopol, HPMC, Tragacanth, semi synthetic celluloses, synthetic celluloses, and mixtures thereof;
      the ratio of the obnoxious or stench causing natural compound to the polymer is in the range of 10:1 to 1:10; and
      the obnoxious or stench causing natural compound is uniformly distributed within a three dimensional gel network of the hydrocolloid polymer.

2. The odor masked nutraceutical or dietary supplement formulation as claimed in claim 1, wherein the obnoxious and stench causing natural compound is the extract of *Valerian officinalis*, the extract of *Valerian officinalis* comprising 0.01% to 30% total valerenic acids.

3. The odor masked nutraceutical or dietary supplement formulation as claimed in claim 1, wherein the odor masked formulation is mixed with at least one additional ingredient selected from the group consisting of flavoring agents, sweeteners, effervescent materials, and pharmaceutically or nutraceutically accepted excipients, diluents or carriers.

4. The odor masked nutraceutical or dietary supplement formulation as claimed in claim 1, where in the odor masked formulation is formulated into an oral dosage form selected from the group consisting of chewable tablets, orodispersible tablets, capsules, dry syrups, dry powders for suspension, suspensions, disintegrating tablets, fast dissolving tablets, and sachets.

5. An odor masked nutraceutical or dietary supplement formulation, comprising an obnoxious or stench causing natural compound and a hydrocolloid polymer;
   wherein:
      the obnoxious or stench causing natural compound is selected from the group consisting of a valerenic acid, an extract of a plant of the genus *Valeriana*, an extract of *Murrava koenigii*, an extract of *Moringa oleifera*, and combinations thereof;
      the hydrocolloid polymer is a hydrocolloid polymer gum or a polyelectrolyte containing gum;
      the ratio of the obnoxious or stench causing natural compound to the hydrocolloid polymer is in the range of 10:1 to 1:10; and
      the obnoxious or stench causing natural compound is uniformly distributed within a three dimensional gel network of the hydrocolloid polymer.

6. The odor masked nutraceutical or dietary supplement formulation as claimed in claim 5, wherein the hydrocolloid polymer is selected from the group consisting of Guar gum, Gum acacia, Gum Kondagogu, Gum Karaya, Xanthum gum, carrageenan, sodium alginate, locust bean gum, gum ghati, carbopol, HPMC, Tragacanth, semi synthetic celluloses, synthetic celluloses, and mixtures thereof.

7. A process for preparation of the odor masked nutraceutical or dietary supplement formulation as claimed in claim 5, comprising;
   a) solvating of the hydrocolloid polymer with a solvent to obtain a solvated polymer;
   b) Mixing the solvated polymer with the obnoxious or stench causing natural compound to obtain a mixture; and
   c) Drying the mixture to entrap the obnoxious or stench causing natural compound within the three-dimensional polymer network;
      wherein the ratio of the obnoxious or stench causing natural compound to the hydrocolloid polymer is in the range of 10:1 to 1:10.

8. The process as claimed in claim 7, wherein the hydrocolloid polymer gum or polyelectrolyte containing gum is selected from the group consisting of Guar gum, Gum acacia, Gum Kondagogu, Gum Karaya, Xanthum gum, carrageenan, sodium alginate, locust bean gum, gum ghati, carbopol, HPMC, Tragacanth, semi synthetic celluloses, synthetic celluloses, and mixtures thereof.

9. The process as claimed in claim 7, wherein the solvent is selected from the group consisting of water, methanol, ethanol, propanol, isopropanol, acetone, and mixtures thereof.

10. The process as claimed in claim 7, wherein solvating of the hydrocolloid polymer with a solvent is carried out using water as a solvent, and produces a hydrogel.

11. The process as claimed in claim 7, wherein solvating of the hydrocolloid polymer with a solvent is carried out using an organic solvent, and produces an organogel.

12. The process as claimed in claim 7, wherein:
the step of mixing comprises mixing the solvated polymer with the obnoxious or stench causing natural compound to obtain the mixture, wherein the ratio between the obnoxious or stench causing natural compound and the polymer is from 1:10 to 10:1; and
the step of drying the mixture is carried out in a vacuum dryer at 40-800° C.

13. The process as claimed in claim 7, further comprising pulverizing the polymer network, and sieving the pulverized polymer network to obtain the odor masked nutraceutical or dietary supplement formulation.

14. A method of treating a disorder in a subject in need thereof, wherein the method comprises administering to the subject a therapeutically effective quantity of the odor masked nutraceutical or dietary supplement formulation of claim 1;
wherein treating the disorder comprises enhancing sleep; reducing anxiety, stress, or depression; treating insomnia; treating Attention Deficit Disorder (ADD); treating Chronic Fatigue Syndrome (CFS), or treating menopause in said subject.

* * * * *